United States Patent [19]

Fawzi et al.

[11] Patent Number: 4,642,316

[45] Date of Patent: Feb. 10, 1987

[54] PARENTERAL PHENYTOIN PREPARATIONS

[75] Inventors: Mahdi B. Fawzi, Flanders; Anne K. Taylor, Morris Plains, both of N.J.

[73] Assignee: Warner-Lambert Company, Morris Plains, N.J.

[21] Appl. No.: 735,932

[22] Filed: May 20, 1985

[51] Int. Cl.$^4$ ............................................ A61K 31/415
[52] U.S. Cl. ..................................................... 514/398
[58] Field of Search ......................................... 514/398

[56] References Cited

U.S. PATENT DOCUMENTS

| 3,749,779 | 7/1973 | Schneller et al. | 424/273 |
| 4,163,058 | 7/1979 | Stella et al. | 424/273 |
| 4,260,769 | 4/1981 | Stella et al. | 548/112 |

OTHER PUBLICATIONS

Chem. Abst. 85-25322z (1976).
Chem. Abst. 91-193312p (1979).

*Primary Examiner*—Stanley J. Friedman
*Attorney, Agent, or Firm*—Sandra M. Person

[57] ABSTRACT

Useful parenteral phenytoin preparations can be made using certain complexes of phenytoin or phenytoin sodium.

13 Claims, No Drawings

PARENTERAL PHENYTOIN PREPARATIONS

BACKGROUND

Phenytoin is 5,5-diphenyl-2,4-imidazolidinedione. It is a well-known pharmaceutical agent having anticonvulsant and antiepileptic activity. Its preparation is described in U.S. Pat. No. 2,409,754.

Due to phenytoin's poor solubility in water, phenytoin sodium, of empirical formula $C_{15}H_{11}N_2NaO_2$, which is more soluble, is employed in the preparation of injectable solutions of the drug. In order to stabilize solutions of phenytoin sodium, it is conventional to employ aqueous alcoholic solvent systems. One conventional component of such systems, propylene glycol, has been associated with undesirable side effects.

The need arose for stable aqueous preparations based on phenytoin which did not contain potentially dangerous solvents, e.g., propylene glycol.

THE INVENTION

It has been discovered that certain derivatives of the compound phenytoin sodium $C_{15}H_{11}N_2NaO_2$, produce stable aqueous solutions in the absence of alcoholic solvents such as propylene glycol. These derivatives are complexes produced by contacting phenytoin sodium with one or more water soluble amines or amine salts. The resultant complexes have solubilities in water of 70 mg/ml or more. Thus, the level of phenytoin available in parenteral formulations containing them can easily meet or exceed required doses. The normal concentration of phenytoin in conventional solutions is generally on the order of 50 mg/ml, with dosages of about 100 to about 300 mg/dose being typical.

In a preferred embodiment, choline hydroxide solution or ethylenediamine/sodium hydroxide solution is reacted with phenytoin sodium. Following dissolution using additional water via, e.g., sonification or shaking, a dilution with more water and filtration are performed.

The resultant solution can be lyophilized. The lyophilized product is readily reconstituted with water. Such reconstituted solutions, which have a pH of about 11.4, can be diluted with normal saline or 5% dextrose without the formation of a precipitate.

OBJECTS OF THE INVENTION

It is an object of the invention to provide highly water soluble complexes of phenytoin sodium and to provide pharmaceutical preparations containing them.

It is a further object to provide a process for making highly soluble complexes of phenytoin salts.

It is yet another object to provide stabilized, e.g., lyophilized, products containing the complexes of the invention and to employ such products in pharmaceutical preparations.

ADVANTAGES OF THE INVENTION

The complexes made in accordance with this invention generally exhibit several advantages in drug preparations which phenytoin and phenytoin sodium do not. Phenytoin, because of its low solubility, cannot be effectively used in injectable solutions. It is extremely difficult to ensure uniform dosages when it is used alone in aqueous solutions.

Phenytoin sodium, on the other hand, is more soluble in water, but it rapidly protonates to form phenytoin, which then comes out of solution, resulting in precipitation and clogging of hypodermic needles, especially during intravenous infusion. The alcoholic solvents normally used to stabilize aqueous solutions of phenytoin sodium have been associated with toxic reactions in patients.

The complexes made in accordance with the invention have neither the low solubility of phenytoin nor the sometimes toxic consequences associated with the alcoholic solvents usually used with phenytoin sodium. Their high solubility in water makes parenteral formulations containing them highly useful. For example, they can be diluted with suitable fluid(s) for intravenous infusion.

In addition, lyophilized products and other suitably stabilized products containing the complexes of this invention are storage-stable and can be readily reconstituted with water.

Other objects and advantages of the invention will become apparent after a consideration of the following description.

DESCRIPTION OF THE INVENTION

Phenytoin and phenytoin sodium are well-known compounds. They are described in *The Merck Index*, 10th ed. (1983) at pages 1054 and 1055.

The invention is concerned with novel derivatives which result from the contacting of at least one of phenytoin and phenytoin sodium with certain "complexing agents". By "complexing agents" is meant compounds which, when contacted with phenytoin and/or phenytoin sodium yield materials which do not have the solubility problems generally associated with phenytoin or its salts. While not wishing to be limited to any particular theory, applicant has characterized these materials as "complexes." They may in fact be simple solutions and the agents solvents for the phenytoin or phenytoin salt, e.g., phenytoin sodium. Alternatively, they may be salts of the phenytoin.

Pharmaceutical preparations, including reconstitutable lyophilized products, can be made using these complexes. Such preparations can contain one or more other excipients, such as surfactants, crystal growth inhibitors, and the like.

The basic complex-forming reaction is believed to take place upon the contacting of phenytoin or phenytoin sodium with one or more complexing agents under suitable conditions. By "suitable conditions" is meant the employment of appropriate reagents—e.g., buffers and/or pH modifiers—to ensure adequate water solubility.

Useful complexing agents are selected from a group of compounds which include, among others, amino acids, amines and amine salts such as: triethanolamine, ethylene diamine, ethanolamine, choline, arginine and meglumine. Mixtures are operable.

For example, when choline is the complexing agent it can be used as a buffer solution containing choline chloride/hydroxide. A useful buffer solution can be made by contacting aqueous choline hydroxide with hydrochloric acid. The hydrochloric acid is employed to lower the pH of the complexing reagent to a value in the range of about 11.4 to about 12.5. It has been observed that this pH is optimal for the stable solutions of the invention.

While hydrochloric acid has been mentioned as suitable for modifying the pH of the aqueous complexing reactant, it should be noted that other inorganic and/or organic acidic substances are also useful. Other useful acidic reagents include phosphoric acid, acetic acid and the like. Mixtures of such acidic substances can be employed.

When the pH is to be raised one or more suitable basic substances can be added. Useful basic substances include ammonium hydroxide, sodium phosphate, sodium hydroxide and the like. Mixtures of basic substances are operable.

After the complexing agent has been suitably prepared, e.g., by buffering a solution of same to the desired pH, it is contacted with the phenytoin. The resultant reaction—using choline hydroxide and phenytoin sodium as models—is believed to be:

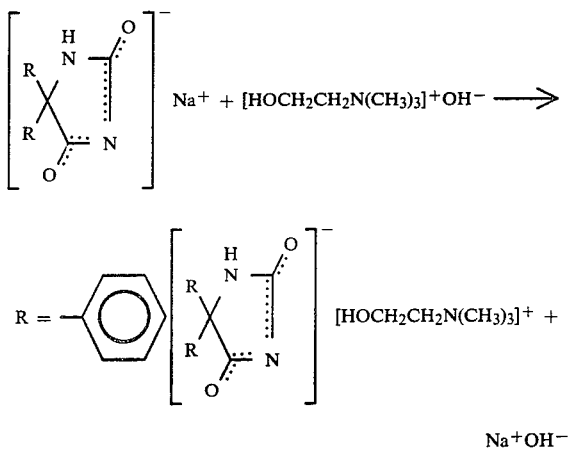

While stoichiometric quantities of the reactants are preferred, the use of an excess of either reactant can be tolerated. Generally, the ratio of complexing agent to sodium phenytoin will be about 3.0:1 to about 1:2.0.

The reaction product is believed to be a complex or salt containing a phenytoin residue as the anionic moiety, and, when choline is the complexing agent, a choline residue as the cationic moiety. The resultant compound, e.g., phenytoin choline, is salt-like in that it is readily soluble in water.

Following the contacting of the phenytoin and the other component, the product is dissolved in more water via suitable solution techniques, e.g., sonication, shaking and the like. The resultant solution is subject to suitable recovery techniques, e.g., filtration, centrifugation and the like, to remove unwanted by-products and unreacted starting materials. Filtration is preferred as a method for sterilizing the product.

The final solution can be used as is in injectable preparations. Depending upon the dosage level desired, it may be further diluted with water or other aqueous media, e.g., dextrose, saline or other conventional solutions. Mixtures of diluents are operable.

The final solution can be subjected to freeze drying or other conventional techniques to put it in a form which is more easily handled and/or stored than is the aqueous solution. If it is lyophilized, the solutions of amine-/phenytoin or amine salt/phenytoin produced in accordance with the invention can be reconstituted using various conventional diluents. Water and aqueous solutions of dextrose or saline are preferred diluents.

The pH of the final solutions in the presence or absence of additional excipients will preferably be from about 11.4 to about 12.5.

While the use of alcoholic diluents should be avoided due to toxicity considerations, the use of other conventional diluents can be tolerated. Thus, when pharmacological considerations dictate, the substitution of all or part of the aqueous diluents discussed above with one or more non-aqueous diluents is contemplated.

The use of one or more suitable excipients is contemplated.

EXAMPLES

The invention will be better understood after consideration of the following examples:

In the following examples, each solution was filtered through a 0.45 micron Nylon 66 filter after preparation. Other filters of smaller size and of different composition may be used. These formulations may be diluted with 5% dextrose solution (2 ml to 100 ml) without precipitation. Quantities of solubilizing agents may be changed after the optimal formulation is determined.

EXAMPLE I

Phenytoin Sodium/Choline Buffer (1:1) Solutions (1) From Choline Hydroxide. A 50% choline hydroxide solution was diluted to 10% and decolorized by adding charcoal and filtering. To 1.25 g (4.6 mmol) phenytoin sodium was added 6.1 ml (5.0 mmol) of the 10% choline hydroxide solution. This mixture was diluted to 20 ml with water and the solids dissolved with stirring or sonication. The resultant solution was adjusted to pH 11.8–12.0 with concentrated hydrochloric acid and diluted to 25 ml.

This 25 ml solution and others made in accordance herewith are prepared using Epanutin from Parke-Davis Division, Warner-Lambert Company, Holland, Mich.

(2) From Choline Chloride. Choline chloride 640 mg (4.6 mmol) was dissolved in 15 ml water and the pH adjusted to 12°–12.5° with 10 N sodium hydroxide. To this was added 1.25 g (4.6 mmol) phenytoin sodium with stirring. The resultant clear solution was diluted to 25 ml and the pH raised to 12.2 with 10 N sodium hydroxide.

(3) From Choline Chloride and Choline Hydroxide. A 10% choline buffer was prepared from equal portions of 10% choline chloride and 10% choline hydroxide. The 10% choline chloride solution was prepared from 10 g of choline chloride diluted to 100 ml with water. The 10% choline hydroxide solution was prepared by diluting a 50% solution, decolorizing with charcoal, and filtering. Choline hydroxide may also be prepared from choline chloride by ion exchange chromatography.

To 1.25 g (4.6 mmol) phenytoin sodium was added 6 ml (5 mmol) choline buffer and diluted with water to 25 ml. The solids were dissolved with stirring or sonication to give a clear solution of pH 12.4.

This example illustrates an embodiment in which the choline solution is made without adding NaOH or HCl.

EXAMPLE II

Phenytoin Sodium/Ethylenediamine (1:2) Solution

Ethylenediamine (0.58 g, 10 mmol) was dissolved in 20 ml water, added to 1.25 g phenytoin sodium, and sonicated to dissolve the solid. When this clear solution was diluted to 25 ml, it had a pH of 11.6.

EXAMPLE III

Phenytoin Sodium/Arginine Solution

Arginine (1.6 g, 4.6 mmol) was dissolved in 20 ml water and added to 1.25 g (4.6 mmol) phenytoin sodium with stirring. One drop of 10 N sodium hydroxide solution was added to complete the dissolution of the solid. After about 30 min. stirring, the pH of the solution stabilized at 11.4–11.6.

EXAMPLE IV

Phenytoin Sodium/Meglumine (1:1) Solution

To 1.25 g (4.6 mmol) phenytoin sodium was added 10 ml of a 10% solution of meglumine (1.0 g, 5.1 mmol), and the solution diluted to 25 ml. When 2 drops 10 N sodium hydroxide were added, the cloudy suspension became clear. After 10 minutes stirring, the pH was 11.5–11.7.

EXAMPLE V

Phenytoin Sodium/Monoethanolamine (1:1) Solution

Monoethanolamine (0.3 g, 4.9 mmol) in 10 ml water was added to 1.25 g (4.6 mmol) phenytoin sodium, and the cloudy suspension was diluted to 25 ml. To obtain a clear solution, 2-3 drops 10 N sodium hydroxide was added and the solution stirred giving a pH of 11.6–11.8.

Reasonable variations, such as those which would occur to a skilled artisan, can be made herein without departing from the scope of the invention.

We claim:

1. A solution suitable for parenteral use consisting essentially of a pharmaceutically effective amount of a complex of at least one drug selected from the group consisting of phenytoin and phenytoin sodium having the empirical formula $C_{15}H_{11}N_2NaO_2$ with a reagent selected from the group consisting of: triethanolamine, ethylene diamine, ethanolamine, choline, arginine, meglumine and mixtures thereof.

2. The solution of claim 1 wherein phenytoin solium is the drug employed.

3. A pharmaceutical preparation containing the solution produced in accordance with claim 2.

4. The pharmaceutical preparation of claim 3 further containing at least one excipient.

5. A lyophilized product derived from the solution of claim 2.

6. A process for prlducing a solution of a drug, which solution is suitable for parenteral use, which comprises the steps of:
   (1) complexing, in an aqueous environment free of alcoholic solvent, at least one drug selected from the group consisting of phenytoin and phenytoin sodium of empirical formula $C_{15}H_{11}N_2NaO_2$ with a reagent selected from the group consisting of: triethanolamine, ethylene diamine, ethanolamine, choline, arginine, meglumine and mixtures thereof.

7. The process of claim 6 wherein the drug employed is sodium phenytoin.

8. The process of claim 7 further comprising the step of:
   (2) lyophilizing the produce of step (1).

9. The process of claim 6 further comprising the step of:
   (2) lyophilizing the product of step (1).

10. The solution produced by the process of claim 6.

11. The solution produced by the process of claim 7.

12. The product produced by the process of claim 8.

13. The product produced by the process of claim 9.

* * * * *